United States Patent [19]
Addiego

[11] Patent Number: 6,109,095
[45] Date of Patent: *Aug. 29, 2000

[54] METAL OXIDE SEMICONDUCTOR CATALYST HYDROCARBON SENSOR

[75] Inventor: William P. Addiego, Big Flats, N.Y.

[73] Assignee: Corning Incorporated, Corning, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/985,123

[22] Filed: Dec. 4, 1997

Related U.S. Application Data

[60] Provisional application No. 60/034,239, Dec. 31, 1996.

[51] Int. Cl.$^7$ .................................................. G01N 7/00
[52] U.S. Cl. ........................... 73/31.06; 73/23.31; 422/88; 422/90; 422/98
[58] Field of Search ................ 73/31.06, 23.31; 422/88, 98, 90

[56] References Cited

U.S. PATENT DOCUMENTS

| | | |
|---|---|---|
| 3,961,987 | 6/1976 | Mund et al. . |
| 4,033,169 | 7/1977 | Fujishiro et al. ...................... 73/31.06 |
| 4,194,994 | 3/1980 | Baresel et al. . |
| 4,535,315 | 8/1985 | Sakai . |
| 4,542,640 | 9/1985 | Clifford ................................. 73/31.06 |
| 4,592,967 | 6/1986 | Komatsu et al. . |
| 4,792,433 | 12/1988 | Katsura et al. ........................... 422/98 |
| 4,892,834 | 1/1990 | Rauh ..................................... 73/31.06 |
| 5,173,166 | 12/1992 | Tomantschger et al. . |
| 5,217,692 | 6/1993 | Rump et al. .............................. 422/98 |
| 5,302,274 | 4/1994 | Tomantschger et al. . |
| 5,338,515 | 8/1994 | Dalla Betta et al. . |
| 5,351,029 | 9/1994 | Huth et al. . |
| 5,389,340 | 2/1995 | Satake ....................................... 422/98 |
| 5,427,740 | 6/1995 | Coles et al. . |
| 5,466,605 | 11/1995 | Glaunsinger et al. ....................... 436/6 |

FOREIGN PATENT DOCUMENTS 2 218 523   11/1989   European Pat. Off. .

*Primary Examiner*—Daniel S. Larkin
*Attorney, Agent, or Firm*—Timothy M. Schaeberle

[57] ABSTRACT

A sensor for selectively detecting HC classes, e.g., alkanes, alkenes and aromatics, in a gas mixture comprising a metal oxide seiniconductor catalyst which is catalytically active for the selective HC classes; the reactions selected from the group consisting of partial oxidation, oxidative dehydrogenation, oxidative coupling and isomerization. Each of these reactions results in imparting a change in the electrical conductivity of the metal oxide which is proportional to the concentration of the HC in the gas mixture. Suitable metal oxide catalysts include $Bi_2O_3$—$MoO_3$, $CoO$—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O$—$V_2O_5$—$MoO_3$, $V_2O_5$—$MoO_3$, $ZnO$—$Fe_2O_3$, $Li_2O$—$MgO$, $V_2O_5$—$P_2O_5$, metal oxide compounds of a spinel or perovskite crystalline structure, and mixtures thereof. A method carried out by the sensor comprises the following steps: (1) contacting the gas mixture with a metal oxide semiconductor catalyst capable of initiating chemisorption and/or at least one catalytic reaction of a selected hydrocarbon class; and, thereafter measuring the resultant change in the electrical conductivity of the metal oxide and thereafter converting the change to the concentration of the total non-methane hydrocarbons in the gas mixture.

29 Claims, 9 Drawing Sheets

METAL OXIDE SEMICONDUCTOR CATALYST HYDROCARBON SENSOR

This application claims the benefit of U.S. Provisional application Ser. No. 60/034,239, filed Dec. 31, 1996, entitled METAL OXIDE SEMICONDUCTOR CATALYST HYDROCARBON SENSOR, by William Addiego.

BACKGROUND OF THE INVENTION

1. Field of the Invention

The present invention relates generally to the technology of measuring the non-methane hydrocarbon concentration in the emissions of an automotive internal combustion engine, and more particularly to the use of metal oxide semiconductor catalysts sensors to monitor the non-methane hydrocarbon oxidation efficiency of an exhaust system's catalytic converter.

2. Description of the Related Art

Catalytic converters have been used on gasoline-fueled automobiles produced in the United States since the mid-1970's for the purpose of promoting the oxidation of unburned hydrocarbons (HCs) and of carbon monoxide (CO). Soon after their introduction, the converters were adapted to promote the chemical reduction of oxides of nitrogen ($NO_x$). At the present time these converters typically employ small amounts of platinum, palladium and rhodium dispersed over a high surface area particulate carrier vehicle which, in turn, is distributed as a thin, porous coating (sometimes called a washcoat) on the wall of a ceramic monolith substrate. The substrate is typically formed by an extrusion process providing hundreds of thin wall, longitudinal parallel open cells per square inch of cross section. These flow-through catalytic devices are housed in a suitable stainless steel container and placed in the exhaust stream under the vehicle downstream from the engine's exhaust manifold.

Under warm, steady-state engine conditions, this conventional catalytic converter containing the precious metal based three-way catalyst (TWC), so called because it simultaneously affects the oxidation of CO and unburned HCs and the reduction of $NO_x$, effectively and efficiently removes most of tie automotive emissions. However, the catalyst system may become malfunctioning after experiencing thermal aging at an unusually high temperature, high exposure to poisoning gases like $SO_2$, and Pb, etc. Furthermore, new emissions regulations require an extended durability of the catalytic converter from 50,000 miles to 100,000 miles. Lastly, as a means to ensure that vehicles meet the certified emission standards throughout the vehicle's operation life, On-Board Diagnostics-II (OBD-II) regulation, as passed by the California Air Resource Board (CARB), calls for continuous monitoring of the efficiency of catalytic converters by direct measurement of the hydrocarbon emission in the exhaust system after the catalyst light-off. Specifically, the monitoring system should be able to indicate when the catalyst system is malfunctioning and its conversion capability has decreased to the point where either of the following occurs: (1) HC emissions exceed the applicable emission threshold of 1.5 times the applicable Federal Test Procedure (FTP) HC standard for the vehicle; and (2) the average FTP Non-methane Hydrocarbon (NMHC) conversion efficiency of the monitored portion of the catalyst system falls below 50 percent.

On the other hand, automotive emissions, before the catalyst system has warmed up to operational temperatures, namely, cold start emissions contribute the majority of pollution from automobiles. Approaches such as, catalytic converters, close coupled to the engine, which heat and begin to function within a few seconds, electrically heated catalytic converters and in-line adsorbers which temporarily store unburned hydrocarbons until the catalytic converter lights off, have all been proven to be effective solutions for the reduction of cold start emissions. Again, OBD-II regulations require that systems be installed in the exhaust system to directly more or the functional status of any of these "cold-start" devices during the lifetime of the car (100,000 miles).

The use of hydrocarbon sensors as on-board catalytic efficiency monitors is a relatively new technological area which has generated increasing interest for the auto industry as a result of OBD-II legislation.

U.S. Pat. Nos. 5,408,215 (Hamburg et al.), 5,265,417 (Visser et al.) 5,444,974 (Beck et al.) each disclose a hydrocarbon sensor system, however each of these three systems utilizes a non-selective or "total" calorimetric catalytic sensor which not only oxidizes the HC but also oxidizes CO and $H_2$. Given the fact that a properly functioning catalytic converter, after light-off, typically produces an exhaust gas hydrocarbon concentration, which is typically on the order of tens (or below) ppm, none of these diagnostic systems are capable of directly and selectively measuring HC concentration in this concentration range. Specifically, these sensor systems do not compensate or account for these interfering gases, especially CO, which are present in concentrations far greater than the HC and therefore interfere with the ability to accurately measure the HC concentration.

SUMMARY OF THE INVENTION

Accordingly, the present invention, in its broadest sense, is directed at a sensor and a method for selectively detecting HC classes, e.g., alkanes, alkenes and aromatics, in a gas mixture. Specifically, the sensor comprises, a metal oxide semiconductor catalyst which is catalytically active for selective HC classes; the reactions selected from the group consisting of partial oxidation, oxidative dehydrogenation, oxidative coupling and isomerization; the method comprising the use of the sensor to detect low concentrations of HC in exhaust gas streams. Each of these reactions results in imparting a change in the electrical conductivity of the metal oxide which is proportional to the concentration of the HC in the gas mixture.

Suitable metal oxide catalysts include $Bi_2O_3$—$MoO_3$, $CoO$—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O_5$—$V_2O_5$—$MoO_3$, $V_2O_5$—$MoO_3$, $ZnO$—$Fe_2O_3$, $Li_2O$—$MgO$, $V_2O_5$—$P_2O_5$, metal oxide compounds of a spinel or perovskite crystalline structure, for example, Mn-doped $ZnFe_2O_4$ and mixtures thereof.

DETAILED DESCRIPTION OF THE INVENTION

The invention is both a HC sensor capable of measuring low HC concentration (ppm) and a process for detecting and measuring HC in an exhaust stream using the sensor.

SENSOR

Figure 1:
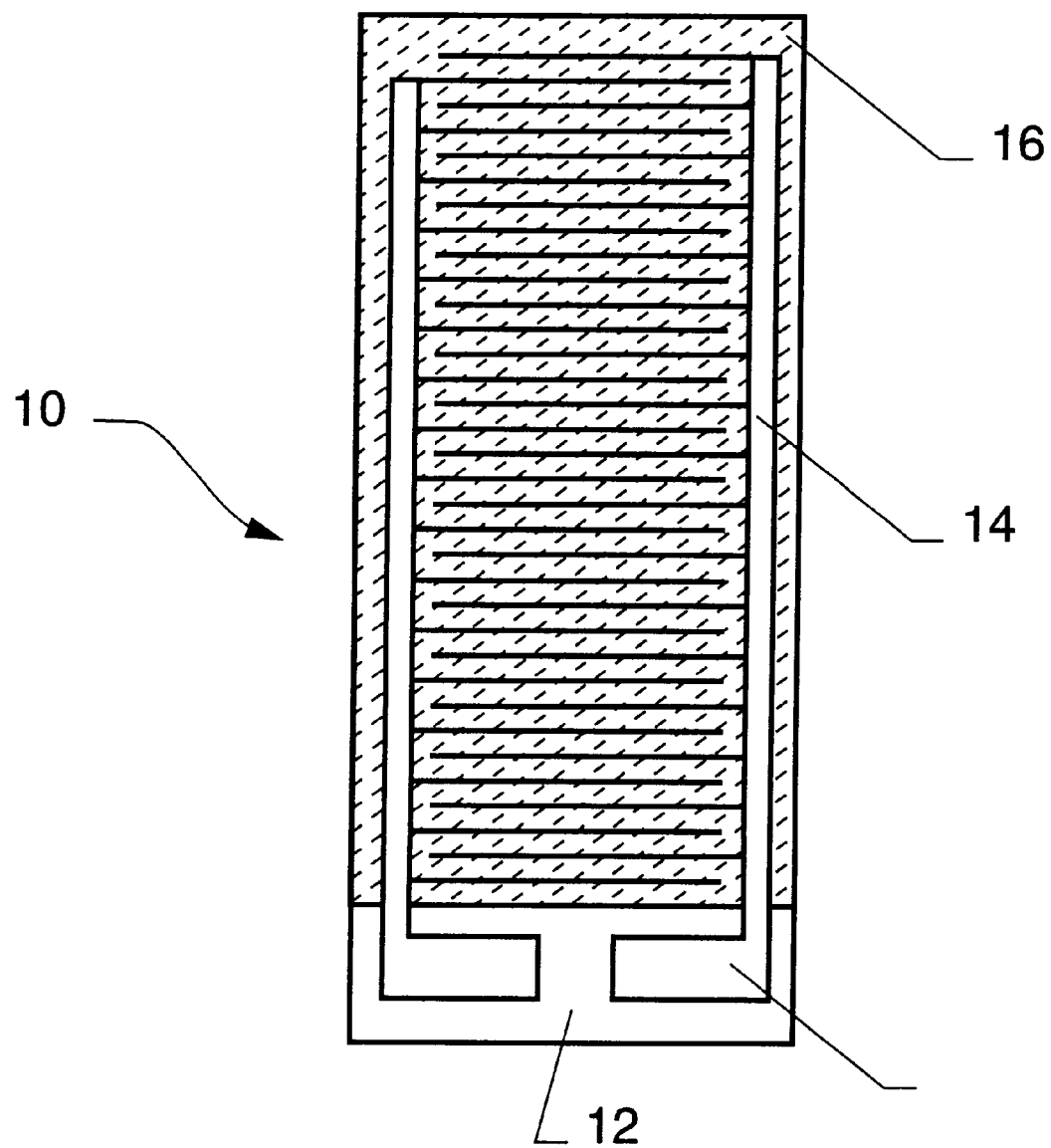
FIG. 1 is a schematic diagram of an embodiment of an inventive sensor for measuring the organic species concentration of an of a gas mixture.

Referring now to FIG. 1 illustrated is a sensor for determining the concentration of an non-methane hydrocarbon (HC) classes in a gas mixture; alkanes, alkenes and aromatics. The sensor 10 comprises a substrate 12 upon which is disposed a means for measuring the resistance change: two interdigitized electrode elements 14 and 16 each having a contact pad 18 and 20. A metal oxide semiconductor catalyst material 22 is deposited onto the substrate and the electrode elements 14 and 16 (not the contact pads 18 and 20, however). It is critical to the proper functioning of the sensor that the metal oxide semiconductor catalyst be selectively active for at least one catalytic reaction of a selected HC class, the classes including alkene, alkane or aromatics. The catalytic reactions are selected from the group consisting of: (1) partial oxidation; (2) oxidative dehydrogenation; (3) oxidative coupling; and, (4) isomerization. Each of these reactions results in imparting a change in the electrical conductivity of the metal oxide which is proportional to the concentration a selected HC class in the gas mixture. The sensor further includes a heater for maintaining the sensor at a sufficient temperature to ensure that the catalytic reaction is initiated and maintained; a resistive heater (not shown) on the underside of the substrate in this embodiment.

Figure 2:
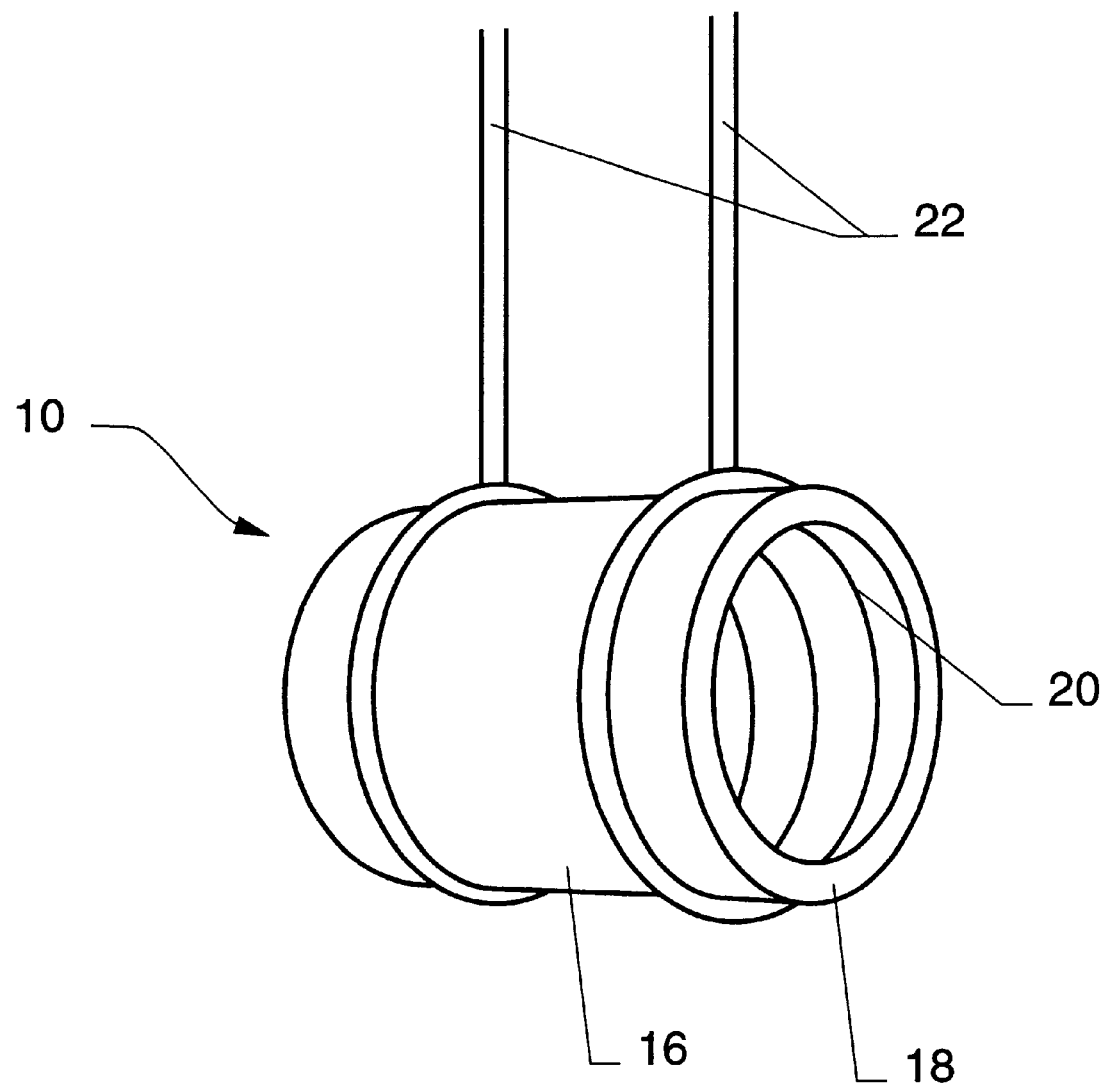
FIG. 2 is a schematic diagram of another embodiment of a sensor for the measuring the organic species concentration of an of a gas mixture.

Referring now to FIG. 2, depicted is another embodiment of the sensor for determining the concentration of a HC class in a gas mixture. The sensor 10 includes a hollow porous substrate 22 having deposited thereon a metal oxide semiconductor catalyst material 16. The sensor further includes a heating coil 24 and electrode leads 26 (e.g., Pt or Au) located on the internal and external surfaces of the hollow substrate 22, respectively.

Metal oxide semiconductor catalyst materials which effectively work in the above sensor embodiments include metal oxides selected from the group consisting of $Bi_2O_3$—$MoO_3$, CoO—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O_5$—$V_2O_5$—$MoO_3$, $V_2O_5$—$MoO_3$, ZnO—$Fe_2O_3$, $Li_2O$—MgO, $V_2O_5$—$P_2O_5$ and mixtures thereof, it is contemplated that other permeations, not listed above, will be effective as well. Other metal oxides which will work in the inventive sensor include metal oxide compounds of a spinel or perovskite crystalline structure, including, for example $ZnFe_2O_4$. In a preferred embodiment the sensor catalyst material comprises a Mn-doped zinc ferrite [$Zn(Fe_{2-x}Mn_x)O_{4-\delta}$], specifically preferred is $ZnFe_{1.85}Mn_{0.15}O_4$; the Mn doping functioning to render the so-formed sensor relatively insensitive to interfering gases, specifically $O_2$, CO and $H_2$.

A critical feature, which will become evident in the description relating to the operation of the sensor, is that the metal oxide semiconductor catalyst possess a highly reactive (or labile) oxygen molecule. Each of these materials is selective for one or more of the selected HC classes, alkane, alkene and aromatics; i.e., the HC classes present will undergo one of the aforementioned catalytic reactions to cause the resistance change in the sensor. It should be empirically determined which of the metal oxides is selective for which of the HC classes; e.g., it is known that $SnO_2$—$Sb_2O_5$ and $Bi_2O_3$—$MoO_3$ are selective for the alkene, propylene, and that ZnO—$Fe_2O_3$ and $SnO_2$—$MoO_3$ are selective for the alkane, isopentane while Mn-doped $ZnFe_2O_4$ is selective for both alkanes and alkenes.

The metal oxide semiconductor catalyst material described above is prepared by any known suitable method including for example, impregnation of oxides, co-precipitation, and direct and reverse strike precipitation. Preferably, the preparation of the spinel semiconductor catalyst materials involves the complexing of a nitrate salt with an acid solution. The catalyst mixture is then calcined at the appropriate temperature suitable for the particular catalyst mixture to form a catalyst powder. Thereafter, the so-formed catalyst powder is then ground so as to result in an average particle size of about less than 3 microns. The ground catalyst powder is then combined with a binder material (not more than 30% by weight of total weight of the metal oxide catalyst) and added to a sufficient amount of alcohol to form an alcoholic slurry; acceptable binders include glass powders and silicon-containing compounds such as tetraethyl silicate, colloidal silica, silicon alkoxide or an appropriate silicon.

Suitable substrate materials, upon which the electrodes are printed and upon which the catalytically active material is deposited and activated, include any dense low surface-area refractory ceramic material; e.g., alumina, titania, zirconia, minerals such as synthetic mnica, and composite refractories such as sodium-silicon aluminum oxide. Substrates comprised of alumina are however, preferred.

It is contemplated that catalyst powder preparation, including grain size and porosity, sensor fabrication and sensor activation each contribute to the behavior and quality of the so-formed sensor. As such, it is important to empirically determine the best powder preparation, fabrication, and activation procedures which should be utilized for each different sensor type and composition.

While not intending to limited by theory, the operation of the gas sensor according to the invention is as follows. As mentioned above, each of the metal oxide semiconductor catalysts is capable of initiating an catalytic reaction for a selected HC class; specifically alkanes, alkenes and aromatics. During each of these catalytic reactions an intermediate charged organic species (existing as either an anionic, cationic, or free radical species) is formed and attached to the catalyst metal oxide molecule on the surface of the sensor. It is not necessary for these catalytic reactions to go to completion in forming the specific products, only that there is activity (i.e., chemisorption), and that activity or interaction imparts an elect onic change in the sensor. The presence of this charged species on the surface of metal oxide sensor imparts a change in the conduction band of the catalyst sensor; in other words, this chemelectronic process imparts a change in the electrical conductivity of the catalytic semiconductive metal oxide sensor which is proportional to the concentration of that HC class in the gas mixture.

For example, it is known that propylene, in the presence of $SnO_2$—$Sb_2O_5$ and $Bi_2O_3$—$MoO_3$ metal oxides, is partially oxidized to form acrolein. During the reaction a proton is abstracted from propylene leaving an adsorbed allyl surface group on the surface of the metal oxide; the adsorption of this intermediate species allyl surface group causes the change in the electrical conductivity of the metal oxide. Other by-product intermediate species which may be formed during partial oxidation include aldehydes, ketones, anhydrides and $CO_2$. Subsequently the adsorbed allyl surface reacts with the lattice or structural (or adsorbed surface) oxygen to form acrolein, while at the same time, gaseous oxygen is dissociatively adsorbed onto the surface of the metal catalyst, replacing this metal oxide structural oxygen. The reaction, with the allyl group represented by the "$CH_2$ CH $CH_2$" and the "MO" representative of an adsorbed transition metal oxide compound, is as follows:

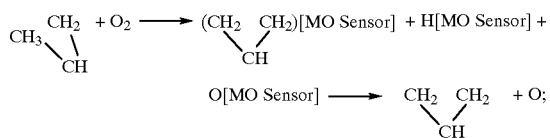

Two further examples of organic catalytic reactions which the inventive metal oxide semiconductive catalysts exhibit include, the oxidative or hydrogenation of both alkanes and alkenes. These reactions, respectively, are as follows:

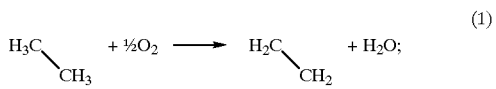

(1)

(2)

As above for the partial oxidation reaction, both the alkane and the alkene reactions result in the formation of the intermediate allyl surface group which is adsorbed and activated by the metal oxide catalyst. As detailed above, it is the formation and activation of this allyl intermediate species which causes the change in the electrical conductivity of the metal oxide and is thus representative of the concentration of the alkane and alkene species in each of the respective oxidative dehydrogenation reactions. It should also be noted that the consumption of surface and lattice oxygen and the subsequent formation of $H_2O$ also contributes to the change in the conductivity of the metal oxide semiconductor. That is, as a semiconductor becomes partially reduced by the removal of structural or lattice oxygen, the conductivity increases because the number of electron carriers increases in the catalyst.

The metal oxides can further include promoter materials which function in the following manner: (1) stabilization of the metal oxide catalyst; (2) promotion of the catalytic activity of the metal oxide catalyst material; and (3) promotion of the selectivity of the metal oxide catalyst material for certain reactions. Suitable promoter materials, chosen depending on the reaction conditions expected, include, for example, precious metals such as rhodium, platinum, palladium, iridium, silver, gold, ruthenium, osmium, and mixtures thereof. Other suitable promoter materials include base elements such as Ti, Fe, Cu and other transition elements, alkali, alkaline earths and rare earth elements.

Regardless of the means used to measure the respective change in the resistance, these measured changes are analyzed to generate an aromatic, alkane or alkene HC class concentration, whichever is being measured; from this single HC class concentration, the total non-methane hydrocarbon concentration can be generated. It is contemplated that a microprocessor based electronic control unit (ECU) can be used to analyze the resistance changes so as to indicate the respective HC class concentration and thereafter the total concentration of unburned non-methane hydrocarbons in the downstream exhaust gas.

In the embodiment described above, when the sensor is positioned downstream of a catalytic converter in an internal combustion engine exhaust stream, and therefore the hydrocarbon concentration of the exhaust gas is determined downstream of the catalytic converter, this measuring of the hydrocarbon concentration is, in actuality, a measure of how well the catalytic converter is functioning; i.e., a system for monitoring the performance of the catalytic converter efficiency. In other words, the concentration of the aromatic, alkene or alkane hydrocarbon present in a exhaust gas portion, downstream of the catalytic converter, directly correlates to the total HC (non-methane) concentration, i.e., the total non-methane HC tail pipe emissions. A measure of how well the catalytic converter is functioning would entail comparing this tail pipe emission to the certified FTP emission standards. As such, this method as a practical and accurate method for monitoring the hydrocarbon catalytic converter efficiency as required by OBD II.

Exhaust gas, for instance, contains greater than 200 species of HCs that can be divided into the alkene, alkane and aromatic species or families. Table I details a representative example of an engine exhaust data from 1991 Buick Park Avenue automobile. The test was conducted in accordance with the FTP procedure for measuring accumulated engine exhaust emissions. Reported in Table I for the exhaust system test conducted are the following hydrocarbon emissions for the entire test cycle, reported in grams per mile: (1) the total non-methane hydrocarbons (NMHC); (2) the total alkene hydrocarbons; (3) the aromatic hydrocarbons; and, (4) the alkane hydrocarbons. Also reported are the percentage (%) of the total NMHC, which each of the hydrocarbon species alkene, aromatic, alkane and aromatic+ alkane comprised. The two stages of the Bag I portion of the test comprised an initial or cold-start test stage (0–60 seconds) and an intermediate stage (60–250 seconds); a Bag II stage followed involving the time period of >250–1372 seconds.

TABLE I

| | Initial Bag I Stage (cold-start: 0–60 secs.) | Intermediate Bag I Stage (60–505 secs) | Bag II Stage (506–1372 secs.) |
| --- | --- | --- | --- |
| Total NMHC (mg) | 1655 | 178 | 80 |
| Alkenes (mg) | 201 | 20 | 11 |
| Aromatics (mg) | 453 | 57 | 19 |
| Alkanes (mg) | 1001 | 101 | 50 |
| Alkane/NMHC (%) | 12 | 11.2 | 13.7 |
| Aromatic/NMHC (%) | 27.4 | 32 | 23.8 |

TABLE I-continued

|  | Initial Bag I Stage (cold-start: 0–60 secs.) | Intermediate Bag I Stage (60–505 secs) | Bag II Stage (506–1372 secs.) |
|---|---|---|---|
| Alkane/NMHC (%) | 60.6 | 56.8 | 62.5 |
| (Aromatic + Alkanes)/ NM HC (%) | 88 | 88.8 | 86.3 |

As is apparent from a study of the data set forth in Table I, car exhaust, during a typical FTP cycle, exhibits a composition in which the alkane, alkene, and aromatic hydrocarbons are fairly consistent from gas sample to gas sample. As such, a selective HC sensor that detects only one of the HC species, aromatics, alkanes or alkenes, with no interference from carbon monoxide or $H_2$ oxidation, is a practical device for measuring the total hydrocarbon concentration as there is a direct correlation between the between the individual species and the total HC concentration.

It is contemplated that a sensor device could be fabricated which is comprised of an array of metal oxide semiconductor catalysts and associated resistance measuring devices, one selective for each of the three major HC classes, alkane, alkene and aromatics. A sensor device which is comprised of $Bi_2O_3$—$MoO_3$ (alkene), $ZnO$—$Fe_2O_3$ (alkane) and MO-vanadates:pyrovanadates (aromatic) would be suitable for this application and the combined resistance change (combination of the three measurements) exhibited by this array sensor would directly correlate to the total non-methane HC concentration without any extrapolation.

METHOD

It follows that placement of the above described sensor results in a method for determining the hydrocarbon concentration in a gas mixture; e.g. placement in the exhaust gas of an internal combustion engine. Simply stated the method comprises the following steps: (1) contacting the gas mixture with a metal oxide semiconductor catalyst capable of initiating chemisorption and/or at least one catalytic reaction of a selected hydrocarbon class, the catalytic reactions being selected from the group consisting of partial oxidation, oxidative dehydrogenation, oxidative coupling and isomerization, wherein the selected hydrocarbon class is selected from the group consisting of alkane, alkene or aromatic hydrocarbons; and, (2) thereafter measuring the resultant change in the electrical conductivity of the metal oxide and converting the change to the concentration of the total non-methane hydrocarbons in the gas mixture.

EXAMPLES

Example 1

100.51 g of $Fe(NO_3)$—$9H_2O$ (Fisher Scientific, Pittsburgh, Pa.) was added to 50 g of deionized $H_2O$ and the mixture was heated and stirred until the metal salt dissolved. 10.61 g of ZnO (Fisher Scientific) was added to the ferric nitrate solution and the heating and stirring continued until the ZnO was thoroughly impregnated. The Fe—Zn mixture was then allowed to dry at approximately 115° C. for about 24 hours and thereafter calcined at 350° C. for about three hours. The dried and calcined Zn—Fe powder was then ground into a fine powder of less than about 3 μm and then calcined again at 750° C. for about 3 hours; allowing a slight air flow during calcining.

5 g of a phosphate glass binder was added to 25 g of the Zn—Fe powder and the mixture was thoroughly mixed. 10.20 g of 200 proof dehydrated ethyl alcohol (Quantum Chemical Co., Cincinnati, Ohio), 2.70 g of 1-butanal (Fisher Scientific), 0.60 g of propylene glycol (Fisher Scientific), and 0.76 g of deionized water are added to the Zn—Fe powder/binder and the mixture is thereafter mixed until the powder has been wetted to form a slurry. Approximately 45 g of 5 mm zirconia grinding media (Tosoh Ceramics, Bound Brook, N.J.) was added to the wetted mixture and the mixture was milled for about 48 hours.

1.1 g of dibutyl pthalate (Aldrich Chemical Co. Inc., Milwaukee, Wis.) and 1.8 g of polyvinyl butyral (Monsanto Chemical Co.) was added to the milled Zn—Fe slurry and this mixture was thoroughly mixed for approximately 15 minutes; the milling media thereafter removed.

An interdigitized electrode-containing alumina substrate was formed in the following manner. A gold-based conductive thick film ink was screen printed and fired onto a 20 mm×87 mm×0.64 mm Kyocera 96% alumina substrate. The screen printing inks consisted of between 60–100 vol % (<10 μm) spherical gold powders (Engelhard Industries) mixed with between about 0–40 vol % (<10 μm) of a borosilicate glass frit. The dry mixture was suspended in a suitable screen printing vehicle and mixed on a 3 roll mill for between about 3.5–15 minutes until the ink was of uniform consistency suitable for screen printing. The inks were then screen printed onto the alumina substrates using a 70 durometer squeegee and a 255 mesh polyester screen with an interdigitized pattern thereby forming an electrode-containing alumina substrate. The so-formed electrode-containing alumina substrate was then dried at 125–150° C. for about 15 minutes and thereafter fired in the following manner: if ink was frit-containing the alumina/electrode body was fired at between 750° C.–800° C. for 5 minutes, and if without frit, it was fired at between 900–1000° C. for 5 minutes.

To fabricate the sensor, the so-formed Fe—Zn slurry was tapecasted onto the electrode-containing alumina substrate using a Pacific Scientific tapecasting apparatus. The alumina substrate/electrode body was cleaned with ethyl alcohol and placed in the apparatus and the Zn—Fe slurry was then tapecasted onto the interdigitized electrode/alumina substrate; taking care not to coat the portion of the electrode which is to serve as the contact. The tapecasted electrode was allowed to dry in air for approximately 2 minutes and thereafter placed in an oven where it was dried at approximately 115° C. for 15 minutes and thereafter calcined for 1 hour at 600° C. Lastly, the sensor was activated by exposure to a hydrocarbon-containing test gas (see example below) maintained at 550° C. for a period of between 4–8 hours.

Figure 5:
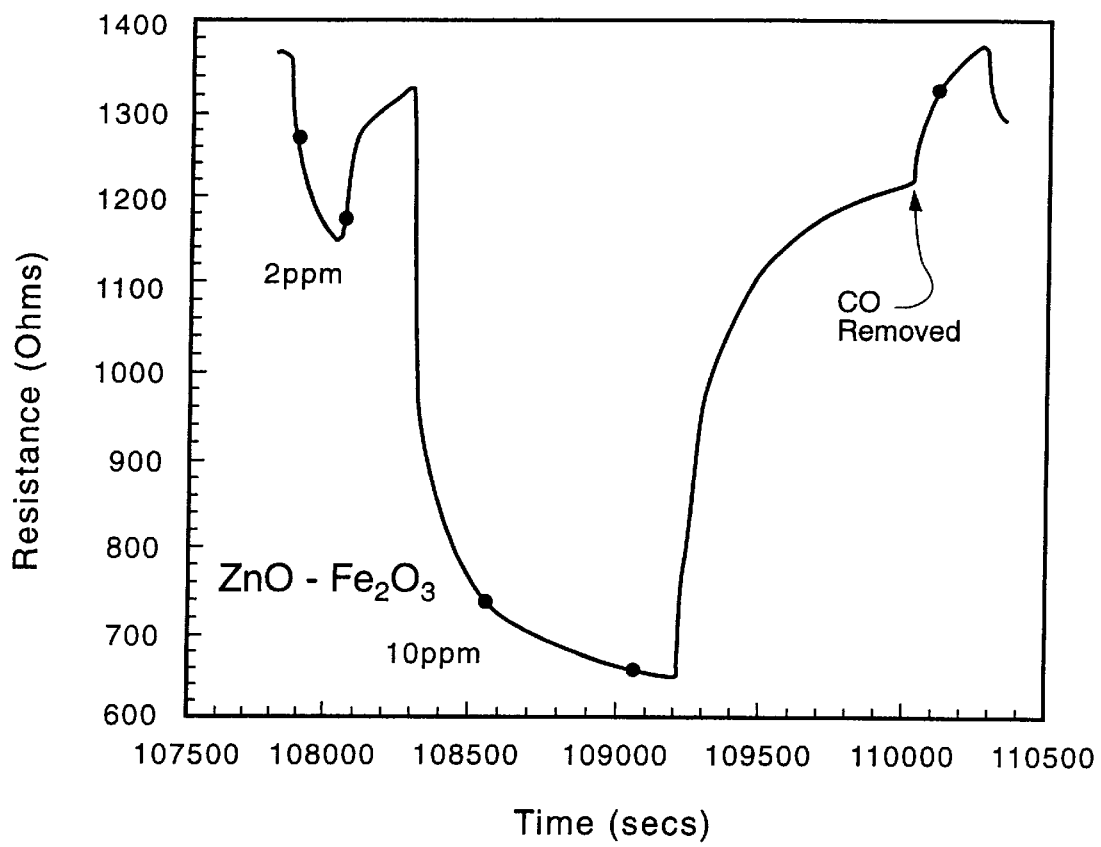
FIG. 5 is a graphical illustration of the variation in resistance over time of a ZnO—$Fe_2O_3$ sensor at 540° C., as a function of varying isopentane concentrations.

The so-formed sensor was tested for HC response by placement in a tubular flow-through reactor by connecting it to a multi-pin feedthrough. The base or initial reaction gas to which certain reaction gases (see below) were added, consisted of 14% $CO_2$, 100 ppm NO, 23 ppm $SO_2$, 0.7% $O_2$, 0.3% $H_2$, with the balance being made up of $N_2$. The test gas combinations were introduced into the reactor, via mass flow controllers, maintaining a constant flow rate of 4500 cc/min, under the following three conditions, corresponding respectively to the FIGS. 3–5 results: (1) increasing isopentane concentrations (2, 5, 10 25 ppm) added to the base gas of above, the $O_2$ gas concentration comprising 0.7% of the base gas so as to achieve a redox ratio of 0.3, furnace maintained at 533° C., and 1000 ppm CO concentration maintained throughout the testing and removed near the conclusion of testing as indicated on FIG. 3; (2) same increasing isopentane concentration addition and redox conditions with a furnace temperature of 540° C., same CO conditions; (3)

same increasing isopentane concentration addition, a reduced $O_2$ amount (0.05% of the total) sufficient to achieve stoichiometric conditions, a furnace temperature of 543° C., and 3080 ppm CO maintained and removed near the conclusion of testing as indicated on FIG. 5.

Figure 3:
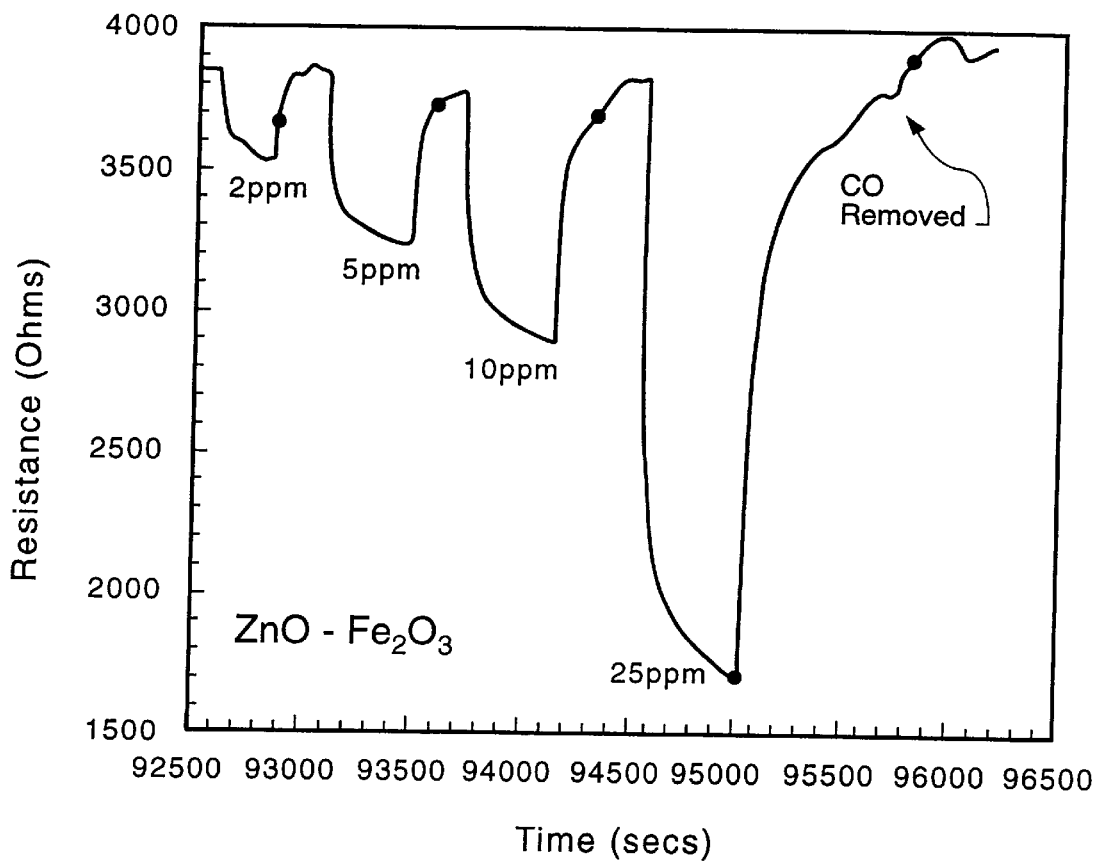
FIG. 3 is a graphical illustration of the variation in resistance over time, of a $ZnO$—$Fe_2O_3$ sensor as a function of varying isopentane concentrations.
Figure 4:
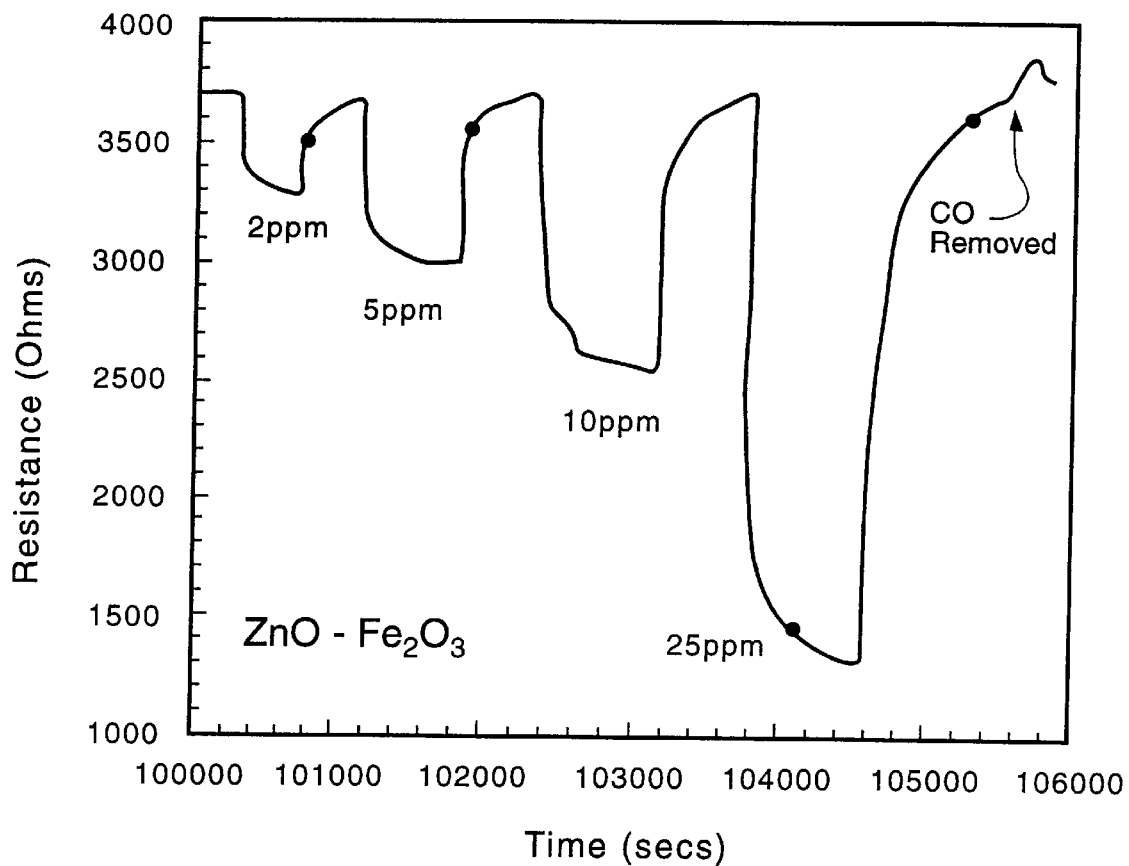
FIG. 4 is a graphical illustration of the variation in resistance over time, of a $ZnO$—$Fe_2O_3$ sensor at 533° C., as a function of varying isopentane concentrations.

An examination and comparison of FIGS. 3–5 reveals the following: (1) the ZnO—$Fe_2O_3$ sensor exhibits sufficiently high sensitivity (for 2 ppm isopentane) regardless of furnace temperature or redox conditions—resistance changes on FIGS. 3–5 as a result of 2 ppm isopentane of 9, 12 and 15%, respectively; (2) very little increase in the baseline resistance as a result of the removal of the CO species in all three tests, thus indicating that the sensor is relatively inactive for, and therefore subject to very little interference from, the CO species.

Figure 6:
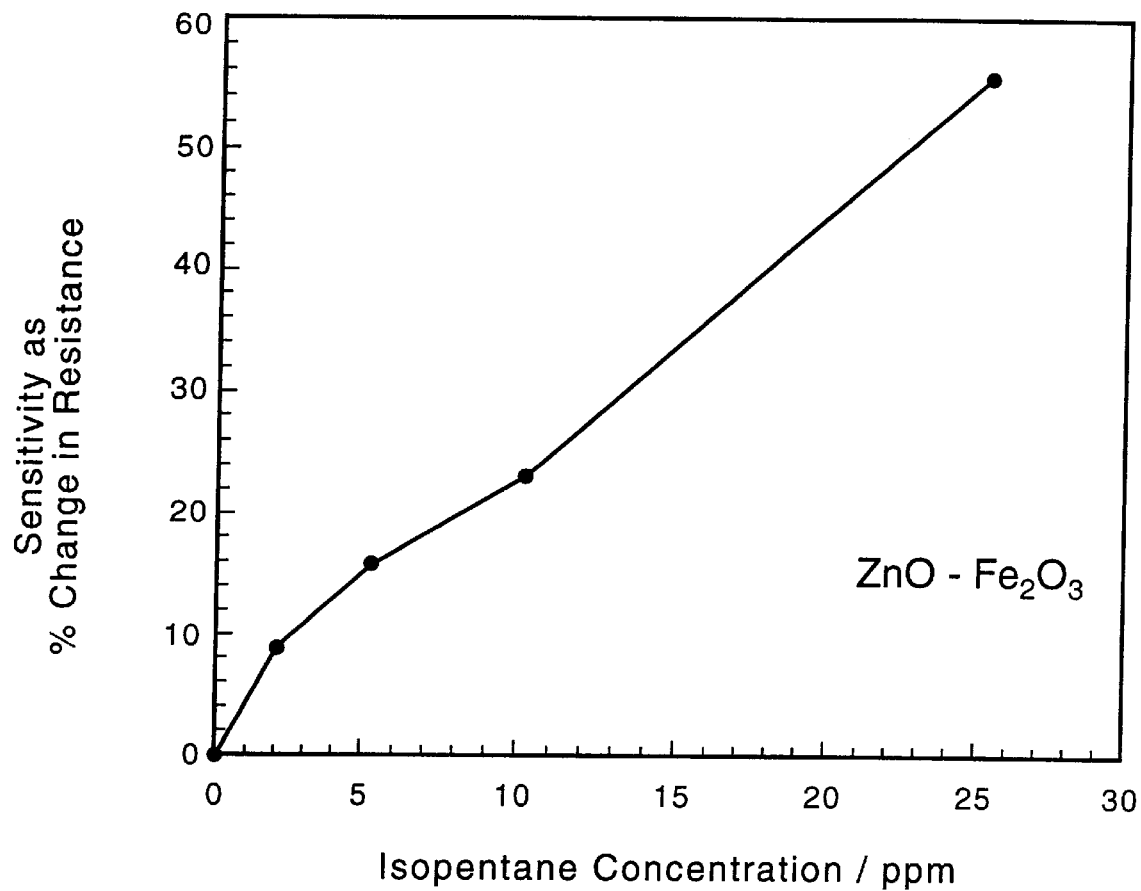
FIG. 6 is a graphical illustration of the percentage change in the resistance of a ZnO—$Fe_2O_3$ sensor at 543° C., as a function of increasing isopentane concentration.

FIG. 6 is a replot of the results reported in FIG. 5. An examination of FIG. 6 reveals a desirable characteristic of the ZnO—$Fe_2O_3$ semiconductor catalyst sensor; a resistance percentage change which is proportional to an increasing isopentane concentration.

Example 2

A $Bi_2O_3$—$MoO_3$ (1:1 mole ratio) metal oxide semiconductive catalyst having interdigitized electrodes was formed in manner similar to above; i.e., formation of a Bi—Mo catalyst slurry and the screen printing of Pt electrodes in an interdigitized pattern onto an alumina substrate and the subsequent tape casting of the electrode-containing alumina substrate with a slurry comprised of the catalyst powder.

As before, the sensor was tested for HC response by placement in a tubular flow-through reactor, and by adding a reaction or test gas to the initial or base gas Specifically, increasing amounts of propylene were added; one testing condition involved the inclusion of 10,000 ppm CO, while CO was absent in the other. The furnace was heated to temperatures of 375 and 430° C., for each of the two gas CO conditions.

Figure 7:
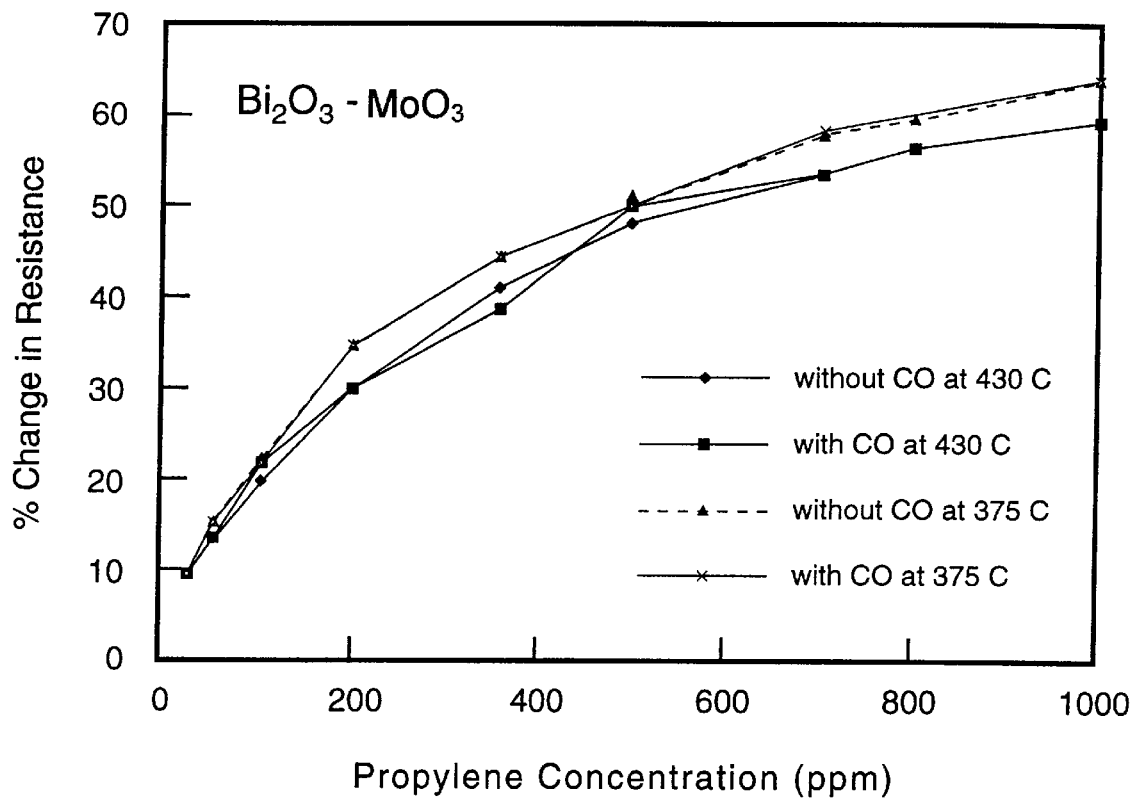
FIG. 7 is a graphical illustration of the percentage chancre in the resistance of a $Bi_2O_3$—$MoO_3$ sensor as a function of the increasing propylene concentration.

FIG. 7 illustrates the percentage resistance change of the as a function of the increasing propylene (alkene) concentration; resistance change percentage calculated is defined as resistance change of the sensor divided by the baseline or starting resistance of the sensor. An examination of the graph illustrates that the resistance change of the sensor is proportional to increasing propylene concentration and that the bismuth molybdate metal oxide exhibits little if any sensitivity to the CO; little if any interference from CO.

Example 3

Figure 8:
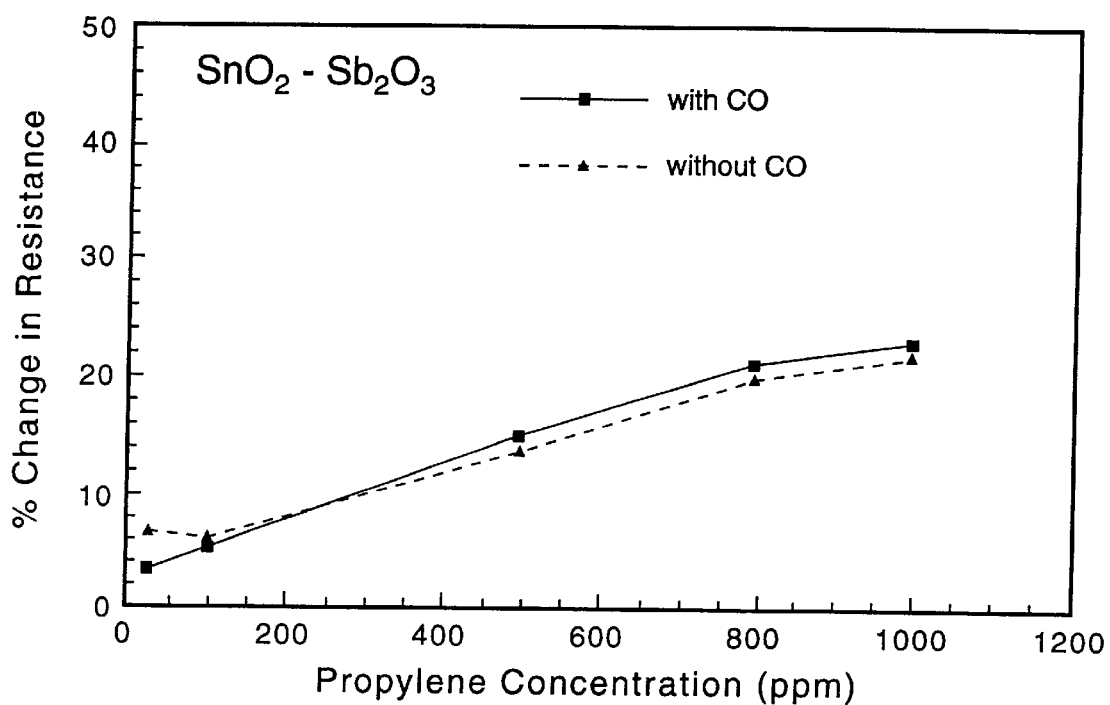
FIG. 8 is a graphical illustration of the percentage change in the resistance of a SnO—$Sb_2O_5$ sensor as a function of the increasing propylene concentration.

A tin-antimonate ($SnO_2$—$Sb_2O_5$) metal oxide semiconductor catalyst sensor was formed in a manner similar to that above and tested, as described above; a minor test change being that the furnace was heated to 330° C. Increasing amounts of propylene were again added to the base gas, which included 1000 ppm CO throughout the testing to test the sensitivity; the CO constituent was removed near the end of the testing at the position indicated. FIG. 8 reveals a similar effect as was observed for the bismuth molybdate sensor above; the $SnO_2$—$Sb_2O_5$ metal oxide semiconductor sensor exhibits a resistance change which is proportional to the increasing propylene concentration and little if any sensitivity to 1000 ppm CO gas introduced.

Comparison Example 1

Figure 9:
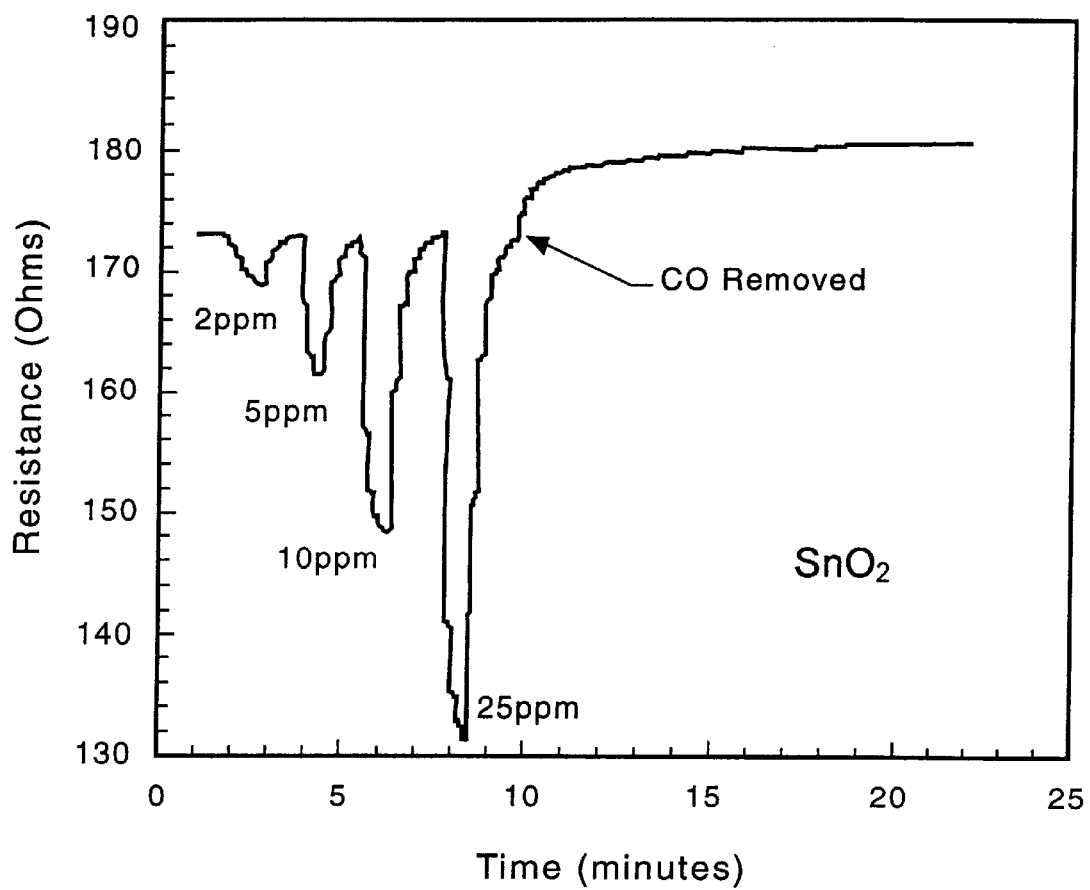
FIG. 9 is a graphical illustration, for comparison, of the variation in resistance over time of a $SnO_2$ sensor as a function of varying isopentane concentrations.

A tin oxide ($SnO_2$) sensor was formed in a manner similar to that above and tested, as described above; a minor testing difference involved heating the furnace to 560° C. and removing the presence of 1000 ppm CO, which was initially introduced, approximately 10 minutes into the test. As before, resistance changes resulting from 2, 5, 10, 25 ppm of added isopentane are clearly seen on the FIG. 9 graphical illustration. However, an examination of the FIG. 9 reveals that this tin oxide material exhibited a much lower sensitivity to 2 ppm of isopentane than above; 9–15% sensitivity for ZnO—$Fe_2O_3$ versus approximately 2% for the SnO sensor. Furthermore, the removal of the CO causes the baseline resistance to rise to 180 ppm (from 174 ppm), thus revealing that 1000 ppm concentration CO has a substantially larger effect, and thus more interference, on the SnO sensor than on the above ZnO—$Fe_2O_3$ and $SnO_2$—$MoO_3$ sensor examples.

Although the now preferred embodiments of the invention have been set forth, it will be apparent to those skilled in the art that various changes and modifications may be made thereto without departing from the spirit and scope of the invention as set forth in the following claims.

I claim:

1. A sensor for determining the concentration of the hydrocarbon in a gas mixture comprising:
   a metal oxide semiconductor catalyst, the metal oxide semiconductor catalyst being selectively active for chemisorption and/or at least one catalytic reaction of a selected hydrocarbon class and substantially inactive to interfering gases including $O_2$, CO and $H_2$, the catalytic reactions being selected from the group consisting of partial oxidation, oxidative dehydrogenation, oxidative coupling and isomerization, and capable of imparting a change in the electrical conductivity of the metal oxide which is proportional to the concentration of the total non-methane hydrocarbons in the gas mixture, wherein the selected hydrocarbon classes are selected from the group consisting of alkane, alkene or aromatic hydrocarbons.

2. The sensor of claim 1 wherein the metal oxide semiconductor catalyst is selected from the group consisting of $Bi_2O_3$—$MoO_3$, CoO—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O_5$—$V_2O_5$—$MoO_3$, $V_2O_5$—$MoO_3$, ZnO—$Fe_2O_3$, $Li_2O$—MgO, $V_2O_5$—$P_2O_5$, and metal oxide compounds of spinel or perovskite crystalline structure and mixtures thereof.

3. The sensor of a claim 2 wherein the metal oxide semiconductor catalyst comprises $SnO_2$—$Sb_2O_5$ and the selected hydrocarbon class is alkenes.

4. The sensor of claim 2 wherein the metal oxide semiconductor catalyst comprises $Bi_2O_3$—$MoO_3$ and the selected hydrocarbon class is alkenes.

5. The sensor of claim 2 wherein the metal oxide semiconductor catalyst comprises $SnO_2$—$MoO_3$ and the selected hydrocarbon class is alkanes.

6. The sensor of claim 2 wherein the metal oxide semiconductor catalyst comprises ZnO—$Fe_2O_3$ and the selected hydrocarbon class is alkenes.

7. The sensor of claim 2 wherein the metal oxide semiconductor catalyst comprises Mo-vanadates or Mo-pyrovanadates and the selected hydrocarbon class is aromatics.

8. The sensor of claim 2 wherein the sensor further includes a precious metal promoter selected from the group consisting of rhodium, platinum, palladium, iridium, silver, gold, ruthenium, osmium, and mixtures thereof.

9. The sensor of claim 2 wherein the sensor further includes a promoter selected from the group consisting of the base elements such Ti, Fe, and Cu, and transition elements, alkalis, alkaline earths and rare earth elements.

10. The sensor of claim 2 wherein the sensor comprises an array of metal oxide semiconductor catalysts, one each which is selective for alkene, alkane and aromatic species, respectively.

11. The sensor of claim 10 wherein the sensor comprises a mixture of metal oxide semiconductor catalysts, wherein the mixture comprises $Bi_2O_3$—$MoO_3$, $ZnO$—$Fe_2O_3$ and Mo-vanadates:pyrovanadates.

12. The sensor of claim 2 wherein the metal oxide semiconductor catalyst comprises $ZnFe_2O_4$ and the selected hydrocarbon classes are alkenes and alkanes.

13. The sensor of claim 2 wherein the metal oxide semiconductor catalyst comprises $ZnFe_{1.85}Mn_{0.15}O_4$ and the selected hydrocarbon classes are alkenes and alkanes.

14. A sensor for determining the hydrocarbon concentration of a gas mixture comprising:

a metal oxide semiconductor catalyst, the metal oxide semiconductor catalyst being selectively active for chemisorption and/or at least one catalytic reaction of a selected hydrocarbon class and which is substantially inactive towards interfering gases including $O_2$, $CO$ and $H_2$, wherein the catalytic reaction involves the formation of an intermediate charged organic species which imparts a change in the electrical conductivity of the metal oxide which is proportional to the concentration of the total hydrocarbon species in the gas mixture.

15. The sensor of claim 14 wherein the catalytic reaction is selected from the group consisting of partial oxidation, oxidative dehydrogenation, oxidative coupling and isomerization.

16. The sensor of claim 14 wherein the metal oxide semiconductor catalyst is selected from the group consisting of $Bi_2O_3$—$MoO_3$, $CoO$—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O_5$—$V_2O_5$—$MoO_3$, $V_2O_5$—$MoO_3$, $ZnO$—$Fe_2O_3$, $Li_2O$—$MgO$, $V_2O_5$—$P_2O_5$, and metal oxide compounds of spinel or perovskite crystalline structure and mixtures thereof.

17. A method for determining the hydrocarbon concentration in a gas mixture comprising:

contacting the gas mixture with a metal oxide semiconductor catalyst capable of initiating chemisorption and/or at least one catalytic reaction of a selected hydrocarbon class and which is substantially inactive towards interfering gases including $O_2$, $CO$ and $H_2$, the catalytic reactions being selected from the group consisting of partial oxidation, oxidative dehydrogenation, oxidative coupling and isomerization, wherein the selected hydrocarbon class is selected from the group consisting of alkane, alkene or aromatic hydrocarbons;

measuring the resultant change in the electrical conductivity of the metal oxide and thereafter converting the change to the concentration of the total non-methane hydrocarbons in the gas mixture.

18. The method of claim 17 wherein the metal oxide semiconductor catalyst is selected from the group consisting of $Bi_2O_3$—$MoO_3$, $CoO$—$MoO_3$, $SnO_2$—$MoO_3$, $TeO_2$—$MoO_3$, $Sb_2O_5$—$V_2O_5$—$MoO_3$, $SnO_2$—$Sb_2O_5$, $Nb_2O_5$—$V_2O_5$—$MoO_3$, $V_2O_5$—$MoO_3$, $ZnO$—$Fe_2O_3$, $Li_2O$—$MgO$, $V_2O_5$—$P_2O_5$, and metal oxide compounds of spinel or perovskite crystalline structure and mixtures thereof.

19. The method of a claim 17 wherein the metal oxide semiconductor catalyst comprises $SnO_2$—$Sb_2O_5$ and the selected hydrocarbon class is alkenes.

20. The method of claim 17 wherein the metal oxide semiconductor comprises $Bi_2O_3$—$MoO_3$ and the selected hydrocarbon class is alkenes.

21. The method of claim 17 wherein the metal oxide semiconductor catalyst comprises $SnO_2$—$MoO_3$ and the selected hydrocarbon class is alkanes.

22. The sensor of claim 17 wherein the metal oxide semiconductor catalyst comprises $ZnO$—$Fe_2O_3$ and the selected hydrocarbon class is alkenes.

23. The method of claim 17 wherein the metal oxide semiconductor catalyst comprises Mo-vanadates or Mo-pyrovanadates and the selected hydrocarbon class is aromatics.

24. The method of claim 17 wherein the sensor further include a precious metal promoter selected from the group consisting of rhodium, platinum, palladium, iridium, silver, gold, ruthenium, osmium, and mixtures thereof.

25. The method of claim 17 wherein the sensor further includes a promoter selected from the group consisting of the base elements such Ti, Fe, and Cu, and transition elements, alkalis, alkaline earths and rare earth elements.

26. The method of claim 17 wherein the sensor comprises an array of metal oxide semiconductor catalysts, one each which is selective for alkene, alkane and aromatic species, respectively.

27. The method of claim 26 wherein the sensor comprises a mixture of metal oxide semiconductor catalysts, wherein the mixture comprises $Bi_2O_3$—$MoO_3$, $ZnO$—$Fe_2O_3$ and Mo-vanadates:pyrovanadates.

28. The sensor of claim 17 wherein the metal oxide semiconductor catalyst comprises $ZnFe_2O_4$ and the selected hydrocarbon classes are alkenes and alkanes.

29. The sensor of claim 17 wherein the metal oxide semiconductor catalyst comprises $ZnFe_{1.5}Mn_{0.15}O_4$ and the selected hydrocarbon classes are alkenes and alkanes.

\* \* \* \* \*